United States Patent [19]

Dziabo, Jr. et al.

[11] Patent Number: 5,213,760

[45] Date of Patent: May 25, 1993

[54] OVERWORN LENS SIGNALING METHODOLOGY

[75] Inventors: Anthony J. Dziabo, Jr., El Toro; Paul S. Ripley, Irvine, both of Calif.

[73] Assignee: Allergan, Inc., Irvine, Calif.

[21] Appl. No.: 838,122

[22] Filed: Feb. 19, 1992

[51] Int. Cl.$^5$ ............................................. A61L 2/16
[52] U.S. Cl. ........................................ 422/37; 422/28; 424/661; 116/201
[58] Field of Search .................... 422/28, 119, 37; 436/904; 424/661; 514/839–840; 116/206, 201; 351/160 R, 160 H, 162, 166, 177

[56] References Cited

U.S. PATENT DOCUMENTS

| | | | |
|---|---|---|---|
| 4,252,421 | 2/1981 | Foley, Jr. | 351/162 |
| 4,457,761 | 1/1984 | Sliger | 8/507 |
| 4,468,229 | 8/1984 | Su | 8/507 |
| 4,553,975 | 11/1985 | So | 8/507 |
| 4,559,059 | 12/1985 | Su | 8/507 |
| 4,616,910 | 10/1986 | Klein | 351/162 |
| 4,654,208 | 3/1987 | Stockel et al. | 424/78 |
| 4,777,684 | 10/1988 | Johnson | 8/507 |
| 4,891,046 | 1/1990 | Wittmann et al. | 8/507 |
| 4,997,626 | 3/1991 | Dziabo et al. | 422/37 |
| 5,011,661 | 4/1991 | Schäfer et al. | 422/30 |
| 5,055,287 | 10/1991 | Kessler | 424/7.1 |

OTHER PUBLICATIONS

*International Eyecare*, "Effect of Chlorine on Tinted Hydrogel Lenses," M. Liebetreu, G. E. Lowther and G. Hammack, vol. 2(10): 525–530 (Oct. 1986).

*Primary Examiner*—Robert J. Warden
*Assistant Examiner*—Timothy M. McMahon

[57] ABSTRACT

A method for signaling a lens user when the user's lenses are overworn. The lenses have applied a handling tint, and the lenses are disinfected in an oxidant solution. The amount of tint added to the lens is such that after soaking the lens for a predetermined period of time in the disinfectant solution, over the expected lifetime of the lens, a noticeable change in the appearance of the handling tint is observed. If the lens is intended to have a fixed lifetime, and the lens is intended to be soaked in a disinfectant solution on a regular basis and for a fixed period of time for the lens lifetime, the amount of the handling tint in the lens can be adjusted such that the handling tint is bleached out or changes color after the lens undergoes regular disinfection within the predetermined lens lifetime.

14 Claims, No Drawings

OVERWORN LENS SIGNALING METHODOLOGY

BACKGROUND OF THE INVENTION

1. Field of the Invention

This invention relates to contact lenses including those contact lenses having a predeterminable normal lifetime. In particular, the present invention relates to methods useful to quickly and effectively identify lense whose wear-life approaches the recommended lifetime of the lens.

2. Related Art

Currently, a major problem with disposable lenses is that patients do not dispose of the lenses pursuant to the manufacture's instructions, that is, by the time the manufacturer believes that the lens has reached its lifetime and has become overworn and should be discarded. Patients often do not dispose of the lenses when the manufacturer indicates they have run their lifetime since many patients perceive lenses to be functional and safe past the recommended wear schedule. This can cause problems with regards to lens performance and the health of the patient due to the fact that an overworn disposable lens is very susceptible to deposit formation, and prolonged extended wear places the patient at a higher risk for ocular complications.

Contact lenses are often periodically disinfected to protect the wearer's eyes from infection and to improve the wearer's comfort. For example, U.S. Pat. No. 4,997,626 to Dziabo and assigned to Allergan, Inc. discloses a method for disinfecting a contact lens comprising contacting the contact lens to be disinfected in a liquid medium with chlorine dioxide present in an amount effective to disinfect the contact lens to be disinfected.

It is well known to apply tints to contact lenses for a variety of reasons. Opaque tints are used to change eye color. Cosmetic tints, also known as "enhancement" tints, are used to enhance the eye color. CIBA Geigy sells a number of cosmetically tinted lenses including those having blue, green and brown tints. Bausch and Lomb manufactures lenses having blue cosmetic tints, among other colors.

Both cosmetic tints and opaque tints are typically applied to the portion of the lens that would cover the iris of the eye.

Another type of tint is a "handling" tint. A handling tint is typically applied to the entire contact lens surface, but at much reduced concentration when compared to an enhancement tint. A handling tint is not intended to enhance or change eye color. Rather, a handling tint is intended to assist the lens user in locating lenses misplaced due to the transparency of the lens material. Due to the slight intensity of color, when the handling tinted lens falls to the bottom of a white lens case, the user can better observe the lens and thereafter handle it. Thus, a handling tint is used for simplicity and ease of lens "handling".

As can be appreciated from the above, the tinting of contact lenses and how the intensity and color of a tint can be varied by varying the amount of the tint in the lens is known. See for example U.S. Pat. Nos. 4,891,046 to Wittmann; 4,559,059 and 4,468,229 to Su; 4,777,684 to Johnson; and 4,252,421 to Foley, Jr. The Wittmann Patent and Su U.S. Pat. No. 4,559,059 note the tendency of the tint in contact lenses to fade or leach out over time or use.

It is known that chlorine has an effect on tinted hydrogel lenses, namely the bleaching of the lenses and the loss of color in the lenses. See "Effect of Chlorine on Tinted Hydrogel Lenses", M. Liebetreu, G. E. Lowther and G. Hammack, *Int. Eyecare*, 2(10): 525-30 (Oct. 1986).

SUMMARY OF THE DETAILED DESCRIPTION

The present invention is directed in general to a method of safeguarding the eyes of contact lens wearers. In particular, the present invention is directed to a method for facilitating the determination as to when to stop wearing a contact lens having a predeterminable lifetime.

The method includes adding an effective amount of a handling tint or other detectable agent to the lens. The amount of the handling tint or other agent is adjusted such that after disinfecting the lens for the normal lens regimen recommended for the lens in a predetermined disinfection solution over almost the entire estimated lifetime of the lens, a detectable change in the appearance of the handling tint is observed. The disinfection solution is preferably an oxidizing solution where a handling tint is used as the agent.

Further provided preferably is a material having a light colored or white background. The lens user is preferably instructed to contact the handling tinted lens with the solution for disinfection, and to thereafter observe the color of the lens against the material having the light colored background. The concentration of tint in the lens can be adjusted such that after a normal regimen of disinfection cycles during almost the entire estimated lifetime of the lens the lens handling tint noticeably or detectably changes in appearance. The user will then be on notice that the lens is approaching or has past its estimated lifetime. The user may then thereafter discard the lens.

DETAILED DESCRIPTION OF THE PREFERRED EMBODIMENTS

A principle discovery of the inventors of the present invention is that the bleaching properties of a chlorine dioxide disinfection solution can be advantageously used to facilitate the determination of when a contact lens has approached its useful lifetime. By adjusting the amount of a handling tint in a lens, the handling tint can be made to bleach away or fade out after the typical number of disinfection cycles employed by the contact lens user according to the recommended disinfection regimen during the estimated lifetime of the lens. By recognizing that the appearance of the handling tint has noticeably changed, the user will be on notice that the lenses are approaching the estimated lifetime of the lens and that the lens should be discarded.

By normal or recommended disinfection regimen, it is meant the number of disinfection cycles and the time period of each disinfection cycle employed by a user in order to maintain the lenses safely disinfected during usage of the lenses. Typically such a regimen is provided by the disinfection solution manufacturer. For example, daily worn disposable soft lenses and the associated disinfection products are typically made to have an 8 hour disinfection cycle. The disinfection solution manufacturer also may sometimes instruct the user to soak the lens in the disinfection solution for another fixed period of time per day.

Instead of adjusting the concentration of the tint in the lens, the present invention may alternatively be practiced by adjusting the chlorine dioxide disinfection solution concentration for a particular concentration of a handling tint in a lens such that the tint noticeably changes color (e.g., brown to yellow or brown to orange) or changes in intensity (greater than 50% by transmittance) when the lens is disinfected according to the normal disinfection regimen over the estimated lifetime of the lens during use by a normal user.

By providing the user with a color coded signal to facilitate the determination of when to stop using the lens, the patient will have a rough approximation as to when to dispose of the lens and to begin using a fresh, new lens. This will facilitate minimizing deposit formation on the lens. The inventive method will also facilitate minimizing the risk that the patient will have ocular complications due to the use of a worn lens. Employing this method will also minimize the chance that a user will wear a lens that has been unacceptably degraded due to being overworn.

The preferable tints in the present invention are handling tints although any oxidizable coloring agent would be appropriate for use and in general any material or agent which can be detected and which can change in detectable appearance by contact with another agent which upon contacting the detectable agent will change the detectable appearance of the detectable agent.

The amount of the handling tint applied to the lens is not intended to change the wearer's eye color. Rather, the amount of the tint is preferably just that amount which will enable the wearer to visually see the lens, during the lifetime of the lens, if the lens falls to the bottom of a white or lightly colored lens case.

Generally the same dyes used for enhancement tints can be used as handling tints in the present application. The most significant difference is that the tint is used at a much lower concentration in the lens polymer (or as a coating on the polymer) than if the tint were being used to provide an enhancement or opaque tinted lens. Therefore, the amount of tint is such that only a faint color is visually observable against a white background.

Lenses that show a change in the appearance of the tint upon disinfection with a chlorine dioxide solution include Allergan ® products Hydron Zero 4 Sofblue and Hydron Zero 6 Sofblue. These lenses have Vat Dye No. 6 (CI No. 69826) handling tint incorporated into the lens polymer.

Although the handling tint should preferably cover the entire lens, it is also within the scope of the present invention that the handling tint be placed in a distinctive annular shape on the lens surface, or just over the iris portion of the lens, or just merely as a distinctive visible dot.

As noted above, a variety of tints can be used. The tint that is used for the Allergan ® Hydron Zero products noted above can be used for the present invention. This dye is shown below:

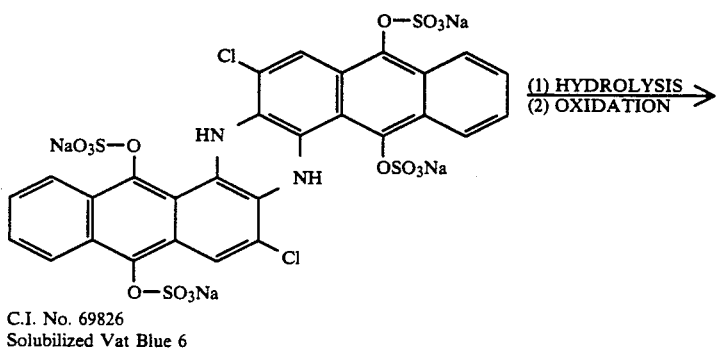

C.I. No. 69826
Solubilized Vat Blue 6

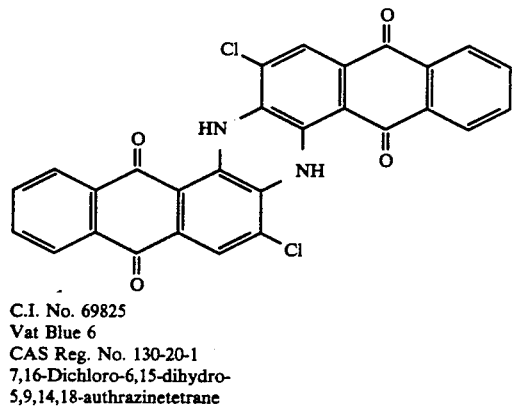

C.I. No. 69825
Vat Blue 6
CAS Reg. No. 130-20-1
7,16-Dichloro-6,15-dihydro-
5,9,14,18-authrazinetetrane Another tint or dye stuff that can be used is shown in the formula below:

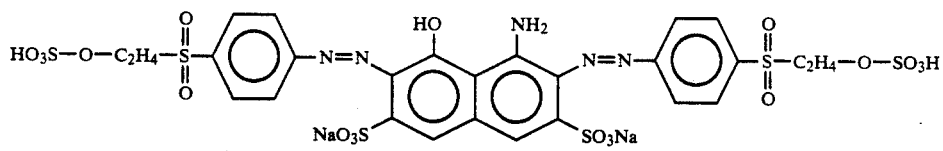

See U.S. Pat. No. 4,468,229.

Other tints that can be used include C.I. Reactive Blue 4 which is used with CIBA ® Geigy Spectrum lenses, and C.I. Reactive Blue 19 and C.I. Reactive Blue 4 as shown below:

C.I. Reactive Blue 19 (Bright blue)

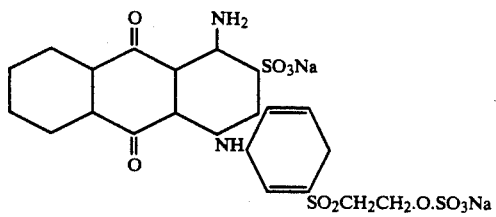

C.I. Reactive Blue 4 (Bright blue)

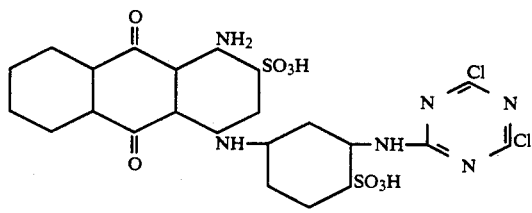

Other dyes or materials are within the scope of the present invention provided that they bleach out or change color or decrease in intensity by at least 50% (by transmittance) during the normal disinfection regimen to just before the end of the estimated lifetime of the lens.

It should be appreciated that the inventors have found that Wesley Jessen opaque tints may not be practical for short lifetime disposable lenses (7-14 day lifetime) as it is difficult to bleach out such tints of such lenses.

There are many known methods for tinting or coloring lenses. See U.S. Pat. No. 4,468,229 and the references cited therein; such patent and references being incorporated into this patent application. One such method of applying a handling tint to a lens is to combine the handling tint and the lens monomer.

There are a variety of disinfection solutions that can be used for the present invention including those that are well known as oxidant solutions. Those include chlorine dioxide, hydrogen peroxide, hypochlorous acid, sodium hypochlorite, perborate, percarbonate, Oxone ® ($2KHSO_5 \cdot KHSO_4 \cdot K_2SO_4$ potassium peroxymonosulfate), dichloroisocyanurate, trichloroisocyanurate, as well as electrochemically generated oxidizers such as chlorine.

Of particular preference is the use of a chlorine dioxide solution wherein chlorine dioxide is present in the range of 0.5 ppm, preferably 0.2-5 ppm, and more preferably 0.2-2.5 ppm. The concentration of chlorine dioxide is at least 0.2 ppm due to the microbiological needs of the lens, i.e., the need to disinfect the lenses and provide safe toxicology an sufficient microorganism kill. It is preferable that the chlorine dioxide concentration be between 0.2 and 5 ppm where the rate of tint loss by chlorine dioxide bleaching is linear. The use of chlorine dioxide solutions for disinfecting lenses is well known; see U.S. Pat. No. 4,997,626 noted above which is incorporated in full into this patent application by this reference.

The concentration of the tint to be incorporated into the lens depends upon the concentration of the chlorine dioxide used for disinfection, the number of and length of the disinfection cycles to be employed by the user during the estimated lifetime of the lens, and the estimated lifetime of the lens. By estimated lifetime, it is meant generally the period of time the lens can be worn without degrading in some manner or affecting the user's eyes in an unsafe manner. Usually the estimated life is provided by the lens manufacturer. For example, Johnson & Johnson Acuvue ® lenses are believed to have an estimated lifetime of 14 days.

Also important to consider is the amount of lysozyme generated by the wearer during use of the lens. It is found that there are some users that generate an unusually large amount of lysozyme which retards the bleaching effect of the chlorine dioxide on the handling tint. Therefore for those persons outside of the norm which generate a higher than normal amount of lysozyme during tearing and use of the lens, the amount of tint in the lens will need to be decreased, or the concentration of chlorine dioxide in the disinfection solution increased. It should thus be appreciated that the present invention is preferably intended to be useful for the normal user having normal amounts of tear and lysozyme production.

The concentration of the selected handling tint to be used in the lens can readily be determined by routine testing. For example, one could employ or prescribe or instruct to disinfect the lenses during the normal regimen a standard chlorine dioxide oxidant solution of 2.5 ppm chlorine dioxide with a lens whose lifetime has been estimated to be no more than 14 days with a disinfection regimen of daily overnight (8 hour) disinfection soaks. Therefore, preferably, the lens is tinted with a concentration of tint such that just before the end of 14 one-hour soaking periods (e.g., about the 12th day), there is a noticeable change in the lens appearance by color change or intensity. Preferably at the 14 day period (12th day preferred) the lens has noticeably changed color, or at least 50%, preferably at least 75% and more preferably substantially all of the lens tint (by transmittance), has been bleached out. In such latter case, the user will be on notice that the lens has approached its lifetime as the lens will be difficult for the user to locate in a white-bottomed lens container.

The concentration of the tint in lenses is directly proportional to UV absorbance. Thus the lenses can be monitored by UV spectroscopy during manufacture until the transmittance (or absorbance) reaches a particular selected value corresponding to the desired level of color intensity, i.e., when the effective tint concentration has been reached. By using such techniques, one skilled in the art can readily determine the proper effective concentration of tint in the lenses and thus also what intensity of tint is necessary to give the proper signaling.

Once the above information is determined by skills well known to those in the art with respect to a 14 day lens, the lens has applied to it either on its surface or within the matrix as discussed above that amount of handling tint that will (1) give a faint appearance against a light or white background and (2) after just before 14 days of use during which 12 one-hour disinfection cycles occurred, a noticeable change in the color of the lens or a more than 50% handling tint intensity loss will be detected by visible observation or by transmittance. The percent of tint loss can be determined by comparison with a color chart having known color/intensity relationship, or by UV-Vis relative transmittance.

It should also be appreciated that if disinfection rate is increased by heating, the required concentration of the tint is more since heating increases the bleaching rate of an oxidant solution.

In general it is preferable that the concentration of tint in the lens is adjusted so that the lens noticeably changes color or intensity over some period, preferably several days, before the lens reaches its lifetime. By providing a lower concentration of tint in the lens than is empirical for the estimated lifetime of the lens, for example 25% less, the lens will change appearance slightly sooner than the lifetime of the lens and thus provide a several day safety cushion between the appearance change warning and the actual end of the lenses lifetime.

One can determine whether the color change is noticeable and the tint intensity loss by comparing the lens color before and after each disinfection cycle against a light colored or white background. The lens color or intensity can be compared by transmittance or by providing the user with a color code or color chart.

For example, the lens user could be provided with a chart showing color changes after each disinfection cycle during the estimated lifetime of the lens for a normal user employing a normal disinfection regimen. The user need then only compare the color of the lens against the color chart to determine how close the lens is to the estimated lens lifetime. (A parallel to this is the typical color coded pool test kit.)

As an example, for Hydron Zero 4 Sofblue, having incorporated therein C.I. Reactive Blue 4, after 31 one-hour disinfection cycles in 2.5 ppm chlorine dioxide, the loss of tint is 20% to 30% (not readily observable). By decreasing the concentration of the handling tint in the lenses, an over 50% or preferably 60% to 90% loss of tint can be observed after 31 cycles.

One embodiment of the methodology of the present invention can be used for short term disposable lenses, for example, those of a 7 to 14 day lifetime. As the length of lens lifetime increases greatly above 30 days, the eye proteins of individuals appear to have a non-linear effect upon the rate of tint loss. Thus, to maintain a linear rate of tint loss, it is suggested that the methodology of the present invention be preferably used with short term disposable lenses.

There are a variety of lenses that can be used in connection with the present invention including those noted above and itemized below:

| LENS | POLYMER/WATER CONTENT |
| --- | --- |
| Hydron Zero 4, Sofblue | polymacon, 38% $H_2O$ |
| Hydron Zero 6, Sofblue | polymacon, 38% $H_2O$ |
| B/L Optima 38, Blue Vis | polymacon, 38% $H_2O$ |
| Ciba Spectrum Visitint, Blue | vifilcon A, 55% $H_2O$ |
| Ciba Focus | vifilcon A, 55% $H_2O$ |
| Ciba STD Visitint, Blue | tefilcon A, 38% $H_2O$ |
| CSI Locator Tint, Blue | crofilcon A, 38% $H_2O$ |
| Softmate B, Blue Vis | bufilcon A, 45% $H_2O$ |
| W/J D3.LT, Green Vis | phemfilcon A, 55% $H_2O$ |
| W/J D4.LT, Blue Vis | ofilcon A, 75% $H_2O$ |
| Coopervision Vantage, Blue Vis | tetrafilcon A, 58%, $H_2O$ |

As another example, with CIBA ® Spectrum lenses, a high water and ionic lens having a blue handling tint, with 1 ppm chlorine dioxide, after 4 cycles, there is not an appreciable visible tint loss. After 9 cycles, there is over a 50% tint loss which is visually significant. Thus, if the CIBA ® Spectrum lenses were intended to be worn for 9 to 12 days, after 9 disinfection cycles, the handling tint would be reduced at least 50% in intensity. The user, upon seeing this reduction, could readily determine that the lens is approaching, or has approached or passed its useful lifetime, and the user can thereby discard the lens.

As another example, CIBA ® soft green lenses, having low water content and being non-ionic, were tested using a 0.5 ppm chlorine dioxide solution under human wear conditions. After 3 overnight (8 hour) disinfection cycles, the handling tint was visibly changed in color. These CIBA soft green lenses are formed of tefilcon 4 polymer.

As another example, when Hydron Zero 4 Sofblue lenses are soaked in a 4 ppm chlorine dioxide disinfection solution, an approximate 40% to 50% tint loss was observed after 10 overnight (8 hour) cycles. With Hydron Zero 4 Sofblue in a 1.5 ppm chlorine dioxide solution, over 50% tint loss was observed after at least 120 cycles.

As yet another example, a disposable lens worn as weekly extended wear, and designed to last one month, is tinted such that it bleaches colorless after four weekly disinfection cycles. The specific concentration of tint and the chlorine dioxide exposure level necessary to produce this effect is readily determined by empirical means well known to those of skill in the art.

Thus, in general, the present invention is directed to a method for safeguarding a contact lens user's eyes. The method comprises the steps of applying to the lens a detectable agent such as an oxidizable handling tint which gives an appearance that can be detected; and contacting the resulting tinted lens with a changing agent such as chlorine dioxide which will change the detectable appearance of the tinted lens by affecting the detectable agent, for example, oxidizing the handling tint. By choosing the detectable agent and changing agent such that as the lens approaches the end of its lifetime the detectable agent changes in appearance, the lens user will be provided with a warning signal that the lens is close to the end of its useful life and should be discarded.

While the description above refers to particular embodiments of the present invention, it will be understood that many modifications may be made without departing from the spirit thereof. The accompanying claims are intended to cover such modification as would fall within the true scope and spirit of the present invention.

The presently disclosed embodiments are therefore to be considered in all respects as illustrative and not restrictive, the scope of the invention being indicated by the appended claims, rather the foregoing description, and all changes which come within the meaning and range of equivalency of the claims are therefore intended to be embraced therein.

What is claimed is:

1. A method for facilitating the determination as to when a contact lens is approaching or has passed the estimated lifetime of the lens, the method comprising:
   adding an effective amount of a tint to the lens to thereby form a tinted lens, the effective amount being such that after periodically contacting the lens with a predetermined solution within a time period approaching the estimated lifetime of the lens, a change in the color of the tinted lens is detected;
   detecting the color of the tinted lens;
   contacting the tinted lens with the predetermined solution; and
   detecting after contact with the solution the color of the tinted lens.

2. The method of claim 1 wherein the solution is an oxidant disinfection solution.

3. The method of claim 2 wherein the solution is a chlorine dioxide solution.

4. The method of claim 1 wherein the solution is a disinfection solution and further including the step of comparing the color of the tinted lens before and after contact with the disinfection solution.

5. The method of claim 4 wherein the lenses are compared against a piece of material having a white surface.

6. The method of claim 1 wherein the lens is disposable.

7. The method of claim 1 wherein the tint is selected from the group consisting of Blue #19, Blue #6 and Blue #4.

8. The method of claim 7 wherein the solution is a chlorine dioxide solution.

9. The method of claim 3 wherein there is present in the solution above 0.2 ppm chlorine dioxide.

10. The method of claim 3 wherein there is present in the solution from 0.2 to 5 ppm chlorine dioxide.

11. The method of claim 3 wherein there is present in the solution from 0.2 to 2.5 ppm chlorine dioxide.

12. The method of claim 1 wherein the lens is Hydron Zero 4.

13. The method of claim 1 wherein the lens is Hydron Zero 6.

14. The method of claim 3 wherein the amount of tint in the lens is determined by:
   determining the concentration of chlorine dioxide to be used to disinfect the lens;
   determining the estimated lens lifetime;
   determining the normal disinfection regimen for the lenses and how long the lenses will be disinfected over the estimated lifetime of the lens; and
   calculating the amount of tint such that after the normal disinfection regimen for the lens to just before the estimated lifetime of the lens, the lens tint will noticeably change in color intensity.

* * * * *

UNITED STATES PATENT AND TRADEMARK OFFICE
CERTIFICATE OF CORRECTION

PATENT NO. : 5,213,760
DATED : May 25, 1993
INVENTOR(S) : Dziabo, Jr., et al

It is certified that error appears in the above-indentified patent and that said Letters Patent is hereby corrected as shown below:

Column 1, Line 9 should read:
methods useful to quickly and effectively identify lenses.

Column 5, Line 67 should read:
provide safe toxicology and sufficient microorganism.

Signed and Sealed this

Twenty-fifth Day of January, 1994

Attest:

BRUCE LEHMAN

Attesting Officer  Commissioner of Patents and Trademarks

UNITED STATES PATENT AND TRADEMARK OFFICE
CERTIFICATE OF CORRECTION

PATENT NO. : 5,213,760
DATED : May 25, 1993
INVENTOR(S) : DZIABO, JR., et al.

It is certified that error appears in the above-indentified patent and that said Letters Patent is hereby corrected as shown below:

Col. 5, delete the formula on line 16 in its entirety and substitute the following:

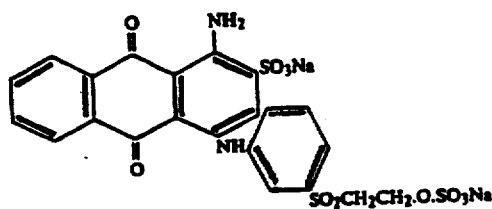

UNITED STATES PATENT AND TRADEMARK OFFICE
CERTIFICATE OF CORRECTION

PATENT NO. : 5,213,760
DATED : May 25, 1993
INVENTOR(S) : Dziabo, Jr., et al

It is certified that error appears in the above-indentified patent and that said Letters Patent is hereby corrected as shown below:

Col. 5, delete the formula on line 26 in its entirety and substitute the following:

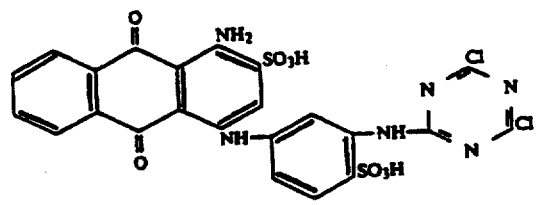

Signed and Sealed this

Twenty-first Day of February, 1995

Attest:

BRUCE LEHMAN

Attesting Officer    Commissioner of Patents and Trademarks